(12) United States Patent
Jo (10) Patent No.: US 6,703,417 B2
(45) Date of Patent: Mar. 9, 2004

(54) AQUEOUS-PRODRUG COMPOUND COMPRISING MOIETY OF PACLITAXEL OR DERIVATIVES THEREOF, METHOD OF PREPARING SAME AND PHARMACEUTICAL COMPOSITION COMPRISING SAME

(75) Inventor: Byung-Wook Jo, Kumho Seangyong Apartment 209-1306, Chugyeong-dong, Seo-ku 502-754 Kwangju-city (KR)

(73) Assignees: Byung-Wook Jo, Kwangju (KR); Kolon Industries, Inc., Kyunggi-do (KR)

( * ) Notice: Subject to any disclaimer, the term of this patent is extended or adjusted under 35 U.S.C. 154(b) by 73 days.

(21) Appl. No.: 10/221,774

(22) PCT Filed: Apr. 13, 2001

(86) PCT No.: PCT/KR01/00618

§ 371 (c)(1),
(2), (4) Date: Sep. 17, 2002

(87) PCT Pub. No.: WO01/78784

PCT Pub. Date: Oct. 25, 2001

(65) Prior Publication Data

US 2003/0050333 A1 Mar. 13, 2003

(30) Foreign Application Priority Data

Apr. 15, 2000 (KR) ......................................... 2000/19873

(51) Int. Cl.$^7$ ................... A61K 31/337; C07D 305/14; C07D 493/00
(52) U.S. Cl. ..................................... 514/449; 549/510
(58) Field of Search ........................ 514/449; 549/510

(56) References Cited

FOREIGN PATENT DOCUMENTS

WO            9324476 A     12/1993

OTHER PUBLICATIONS

Greenwald et al., "Highly water soluble Taxol derivatives: 7-Polyethylene glycol carbamates and carbonates" In J. Org. Chem., 60 (2), pp. 331–336 (1995).

*Primary Examiner*—Taofiq A. Solola
(74) *Attorney, Agent, or Firm*—Birch, Stewart, Kolasch & Birch, LLP

(57) ABSTRACT

Disclosed is an aqueous-prodrug compound comprising paclitaxel or derivatives thereof. The prodrug compound exhibits improved bioavailability.

12 Claims, 4 Drawing Sheets

AQUEOUS-PRODRUG COMPOUND COMPRISING MOIETY OF PACLITAXEL OR DERIVATIVES THEREOF, METHOD OF PREPARING SAME AND PHARMACEUTICAL COMPOSITION COMPRISING SAME

This application is the national phase under 35 U.S.C. §371 of PCT International Application No. PCT/KR01/00618 which has an International filing date of Apr. 13, 2001, which designated the United States of America.

BACKGROUND OF THE INVENTION

(a) Field of the Invention

The present invention relates to a water-soluble prodrug compound comprising a moiety of paclitaxel or derivatives thereof, a method of preparing the same, and a pharmaceutical composition comprising the same. More particularly, the present invention relates to a water-soluble prodrug compound comprising a moiety of paclitaxel or derivatives thereof, exhibiting good bioavailability and reduced side effect by dissolving aids, and a method of preparing the same and a pharmaceutical composition comprising the same.

(b) Related Arts

Paclitaxel (known as taxol) is a compound originally isolated from the bark of the Pacific Yew tree, and a derivative thereof (e.g. docetaxel) is semi-synthetically produced from baccatin III derivatives from the bark of the Pacific Yew tree. These paclitaxel or derivatives thereof has a diterpene structure of formula Formula wherein,
if $R_1$ is $C_6H_6$, $R_2$ is $CH_3CO$, this compound is paclitaxel,
if $R_1$ is $(CH_3)_3CO$, $R_2$ is H, this compound is docetaxel.

The research on the reaction mechanism of paclitaxel isolated by Wall and Wani in 1967 has been widely investigated has found paclitaxel to have strong toxic to cell and anticancer ability, and paclitaxel has been used as an anticancer agent manufactured by Bristol-Myers Squibb Company USA in 1992.

As paclitaxel prohibits mitotic cancer cell division rather than the conventional anticancer agent, it has relatively low toxic to body and strong anticancer ability and it was widely used in the 1990's. This paclitaxel has been approved by the U.S. Food and Drug Administration (FDA) to treat ovarian cancer in 1992, breast cancer in 1994 and Kaposi's sarcoma. Furthermore, paclitaxel is used for treating liver cancer, lung cancer, articula rheumacute, Alzheimer's disease, and a clinical testing of paclitaxel with various drugs have been conducted which is expected to increase the use of paclitaxel.

Paclitaxel is insoluble in water, and it is administrated with surfactants such as Cremophor-El (polyoxyethylated castor oil), or polysorbate. For example, taxol parenteral fluid (Taxol, Birtsol-Myers Squibb) clinically applied used 6 mg of paclitaxel and 527 mg Cremophor-El as a surfactant in 1 ml of 49.7% (v/v) alcohol solution, taxotere parenteral fluid (Rhone-Poulenc Rorer) using docetaxel, paclitaxel derivatives includes 20 mg of docetaxel and 0.5 ml of polysorbate 80 as a surfactant in 1.83 mml of 13% (w/w) alcohol solution.

It was known that the Cremophore-EL or polysorbate as a surfactant causes serious side effect such as hypersensitivity reaction to some patients (Lorence, W., et al, *Agents and actions*, 12, 64–80, 1982). In addition, the use of vegetable oils such as Cremophore-EL causes side effect such as hypersensitive reactions. Furthermore, it is undesirable that materials with high viscosity such as alcohol and Cremophore-EL (it is changed from solution to solid according to ambient temperature) is used in parenteral fluids. The use of organic solvents such as alcohol causes problems such as hemolytic occurrence at injection area and local stimulation.

Due to these reasons, paclitaxel (taxol) produces side effects such as neuropathy, myopathy, myalgia, neutropenis and docetaxel (taxotere) produces unfavorable side effects such as stomatitis, edema and malaise.

Several methods on the development of a water-soluble prodrug compound including paclitaxel have been suggested to reduce such side effects and to improve bioavailbility. Especially, the scientists are concerned about the development of a prodrug compound using polyethyleneglycol (PEG) and actively studied. Recently, Greenwald (Enzon, Inc.) et al synthesized various paclitaxel prodrug with polyethyleneglycol (U.S. Pat. Nos. 5,614,549, 5,880,131 and 5,965,566), and water-soluble prodrug with polyethyleneglycol (U.S. Pat. No. 5,648,506). Chun Li (PG-TXL Company) et al synthesized water-soluble prodrug by reacting paclitaxel with succinic anhydride to prepare 2'-succinyl-paclitaxel and by reacting methyoxypolyoxyethylene amine with 2'-succinyl-paclitaxel (U.S. Pat. No. 5,977, 163). However, it is difficult to produce formulations using these conventional compounds. Paclitaxel prodrug should be rapidly hydrolyzed by an esterase in vivo to generate physiologically active paclitaxel. However, it is known that the conventional paclitaxel prodrug has a long half life time ($T_{1/2}$) in which paclitaxel prodrug is hydrolyzed to generate to paclitaxel, of 1 to 8 hours in rat plasma, the half-life time should be reduced about 10 minutes or less.

SUMMARY OF THE INVENTION

The object of the present invention is to provide a water-soluble prodrug compound including a moiety of paclitaxel or derivatives thereof, which is rapidly hydrolyzed in vivo so that it exhibits improved bioavailability.

Another object of the present invention is to provide a water-soluble prodrug compound including a moiety of paclitaxel or derivatives thereof, which has substantially no side effect caused by dissolving aids.

Still another object of the present invention is to provide a water-soluble prodrug compound which has a short half life time so that it's formulation is easy.

Still another object of the present invention is to provide a method of preparing the water-soluble prodrug compound.

Still another object of the present invention is to provide a pharmaceutical composition including the water-soluble prodrug compound.

These and other objects may be achieved by a water-soluble prodrug compound including a moiety of paclitaxel or derivatives thereof, represented by formula 1.

Formula 1

(wherein,

R is formulas a or b,

<Formula a>

OCH$_3$

<Formula b>

D represents a moiety of paclitaxel or derivatives thereof,

M is an integer of 1 to 6, n is an integer of 10 to 1,000,

X represents O, S or NH, and

R' represents H or CH$_3$)

The present invention further provides a method of preparing the water-soluble prodrug compound including a moiety of paclitaxel or derivatives thereof, represented by formula 1 in which a compound of formula 2 reacts with a polyethylene glycol derivatives compound.

<Formula 2>

<Formula 3>

(wherein,

R is formulas a or b,

OCH$_3$  <Formula a>

<Formula b>

D represents a moiety of paclitaxel or derivatives thereof, m is an integer 1 to 6, n is an integer of 10 to 1,000, X represents O, S or NH, R' represents H or CH$_3$, and

Y is a suitable leaving group such as halogen.)

The compound of formula 2 is prepared by esterifying paclitaxel or derivatives thereof and a compound of formula 4, or prepared by reacting paclitaxel or derivatives thereof with a silyl agent to prepare a compound of formula 5, reacting the compound of formula 5 with a compound of formula 4 to prepare a compound of formula 6, and deprotecting the compound of formula 6 with a weak acid.

<Formula 4>

<Formula 5>

<Formula 6>

(wherein,

R$_1$ is C$_6$H$_6$ or (CH$_3$)$_3$CO,

R$_2$ is CH$_3$CO or H,

Pt is a silyl protecting group,

D' is a moiety of the compound of formula 5,

R' is H or CH$_3$, and

Y is a suitable leaving group such as halogen.)

The present invention provides a pharmaceutical composition including a water-soluble prodrug compound with a moiety of paclitaxel or derivatives thereof, of formula 1 as an active ingredient.

DETAILED DESCRIPTION OF THE INVENTION

The present invention relates a water-soluble prodrug compound including paclitaxel or derivatives thereof. The water-soluble prodrug compound of the present invention is obtained by introducing a new self-immolating linker which is spontaneously decomposed, into paclitaxel and water-soluble polymer and combining water-soluble polymer with the resulting product, and the prodrug compound is rapidly hydrolyzed by an esterase to generate physiologically active paclitaxel.

The water-soluble prodrug compound is represented by formula 1.

<Formula 1> where,

R is formulas a or b,

OCH$_3$ <Formula a>

<Formula b>

D represents a moiety of paclitaxel or derivatives thereof, for example, moiety of docetaxel, m is an integer of 1 to 6, preferably 1 to 3, n is an integer of 10 to 1,000, preferably 10 to 460, more preferably 40 to 230, X represents O, S or NH, and R' represents H or CH$_3$.

The prodrug compound of formula 1 is prepared by reacting a compound of formula 2 with polyethylene glycol compound derivatives of formula 3 in the presence of a solvent such as benzene, toluene or chlorobenzene. At this time, the amount of the polyethylene glycol compound derivatives is suitably 1 to 3 equivalents based on 1 equivalent of the compound of formula 2. The amount of polyethylene glycol compound is less than 1 equivalent, the reaction does not complete, whereas the amount thereof is more than 3 equivalents, the unwanted side reaction occurs.

This reaction is performed in the presence of a reaction-accelerating catalyst, a base and a cation capture. The reaction-accelerating catalyst may be iodine or potassium iodide, and the amount thereof is suitably 1 to 5 equivalents based on 1 equivalent of the compound of formula 2. The base may be sodium carbonate, sodium hydrogencarbonate, potassium hydrogencarbonate, sodium hydroxide, or potassium hydroxide, and the amount thereof is suitably 1 to 5 equivalents based on 1 equivalent of the compound of formula 2. In addition, the cation capture may be crown ethers such as 18-crown-6 ether, and the amount thereof is suitably 0.3 to 5 equivalents based on 1 equivalent of the compound of formula 2.

<Formula 2>

<Formula 3>

(wherein,

R, D, m, n, X and R' have the meanings given above, and

Y is a suitable leaving group such as halogen.)

The compound of formula 2 may be prepared by esterifying paclitaxel or derivatives thereof with a compound with carbonyl group of formula 4 in the presence of a solvent such as methylene chloride, ethylene dichloride, chloroform, carbon tetrachloride, tetrahydrofuran or ethyl ether. The compound with carbonyl group is desirably 1 to 3 equivalents based on 1 equivalent of paclitaxel or derivatives thereof. If the amount of the compound with carbonyl group is less than 1 equivalent, the reaction does not complete, whereas the amount thereof is more than 3 equivalents, the unwanted side reaction occurs. This reaction is performed in the presence of a base such as N,N-diisopropylethylamine, triethylamine or pyridine. At this time, the amount of the base is desirably 1 to 3 equivalents based on 1 equivalent of paclitaxel or derivatives thereof. In this reaction, the reaction occur at 2'-OH of paclitaxel or derivatives thereof.

<Formula 4>

(wherein, R' and Y have the meanings given above.)

Alternatively, the formation of compound of formula 2 may be accomplished by the following procedure. Paclitaxel or derivatives thereof reacts with a silyl agent in a solvent such as dichloromethane to prepare a compound of formula 5.

A silyl group in the silyl agent protects a 2'-OH group of paclitaxel or derivatives thereof, and the silyl agent may be t-butyl dimethyl silyl chloride, trimethyl silyl chloride, trimethyl silyl cyanide, hexa methyl disilazine or trimethylsilyl diethyl amine. The amount of silyl agent is desirably 1 to 3 equivalents based on 1 equivalent of paclitaxel or derivatives thereof. This reaction may be performed by adding paclitaxel or derivatives thereof to a solvent and simultaneously adding a silyl agent, a base and a soluble-aid to a solution of paclitaxel or derivatives thereof. Alternatively, a base is dissolved in a soluble-aid to prepare a base solution and then base solution and a silyl agent are added to a solution of paclitaxel or derivatives thereof. The exemplary of the base may be imidazole, and the soluble-aid may be a silyl agent solution in a solvent such as N,N-dimethylformamide, N,N-dimethylacetamide or dimethyl sulfoxide.

Thereafter, the compound of formula 5 esterification-reacts with the compound with carbonyl group of formula 4 in the presence of a solvent such as dichloromethane, ethylene dichloride, chloroform, carbon tetrachloride, tetrahydrdofuran or ethyl ether to obtain a compound of formula 6. In this step, N,N-diisopropylethylamine, triethylamine or pyridine may be further added. In this reaction, the reaction occur a 7-OH group.

The compound of formula 6 deprotects with a weak acid such as HF, citric acid, acetic acid, polystyrene formic acid, formic acid, or tetraammonium fluoride in the presence of a solvent such as acetonitrile, methanol, tetrahydrofuran or diethylether, to prepare a compound of formula 2. The weak acid is a solution with a concentration of 0.1 to 10% and a solvent may be acetonitrile, methanol or tetrahydrofuran.

<Formula 5>

<Formula 6>

D'—OCOCHY
         ‖ |
         O R'

(wherein, R' and Y have the meanings given above,
R$_1$ is C$_6$H$_6$ or (CH$_3$)$_3$CO,
R$_2$ is CH$_3$CO or H,
Pt is a silyl protecting group,
D' is moiety of the compound of formula 5, and
Y is a suitable leaving group such as halogen.)

The prodrug compound of the present invention is hydrolyzed by an esterase in vivo to convert paclitaxel as an active ingredient. When the prodrug compound of the present invention is hydrolyzed by the esterase, a new self-immolating linker which is spontaneously decomposed, decreases a steric hindrance of paclitaxel during the approach of the esterase so that the prodrug compound is rapidly hydrolyzed and the spontaneous decomposition of the self-immolating linker is rapidly spontaneously decomposed and the conversion from the prodrug to paclitaxel promptly occur.

In the polyethylene glycol derivatives used for preparing the prodrug compound of the present invention, polyethyleneglycol has a linear or branched neutral polymer and various molecular weights, and it has no toxic to human and is safety material which is approved as internally used by FDA. Accordingly, polyethylene glycol group gives water-solubility to the prodrug compound paclitaxel.

Such a high water-solubility (solubility to water: >400 mg/ml) requires no use of surfactants and organic solvents which are reasons causing significant hypersensitivity to patients. Therefore, the prodrug of the present invention has advantages that it has no side effect such as neouropathy. myopathy, myalgia, neutropenia, stomatitis, edema or malaise caused by surfactants and organic solvents used in the conventional prodrug compound (Taxol, Taxotere).

The prodrug compound of the present invention may be useful as active ingredients in pharmaceutical composition for treating breast, ovarian and lung cancers, and Kaposi's sarcoma, and for treating liver cancer, stomach cancer, rheumacute articular, or Alzheimer's disease. The pharmaceutical composition including the prodrug compound as active ingredients of the present invention may further include pharmaceutically acceptable additives.

The present invention is further explained in more detail with reference to the following examples, but the examples are not intended to limit the present invention.

<EXAMPLE>1

Synthesis of 2'-Chloromethyloxycarbonyl Paclitaxel
(1)

Paclitaxel (1.0 g, 1.171 mmol) was dissolved in 10 . of anhydrous methylenechloride. Diisopropylethylamine (307.6 ., 1.76 mmol) was added to the resulting solution and the mixture was cooled to 0. in a ice bath. Chloromethyl chloroformate (167.3 ., 1.76 mmol) was slowly added to the resulting mixture and reacted for 2 hours at 0. The resulting reaction solution was dried under reduced pressure in a rotary vacuum dryer and the residue is recrystalized from ethylacetate/n-hexane to yield 900 mg of a product (81%). $^1$H NMR (300 MHz, CDCl$_3$) . 5.71 (s, 3H, 3'-H, OCOO CH$_2$Cl), 5.48 (d, 1H, J=2.74 Hz, 2'-H); $^{13}$C NMR (75 MHz, CDCl$_3$) . 152.64 (O$\underline{C}$OOCH$_2$Cl)

<EXAMPLE>2

Synthesis of 2'-monomethoxypolyethyleneglycol 5000-succinyloxymethyloxycarbonyl-paclitaxel (2)

2'-chloromethyloxycarbony paclitaxel (250 mg, 0.264 mmol) was dissolved in anhydrous benzene. Monomethoxypolyethyleneglycol 5000-succinate (1.32 g, 0.264 mmol), sodium iodide (79.1 mg, 0.528 mmol), potassium carbonate (109.5 mg, 0.792 mmol), 18-crown-6 ether (34.9 mg, 0.132 mmol) were added to the resulting solution, and the resulting mixture was refluxed for 20 hours. The resulting reaction mixture was cooled to room temperature and the cooled mixture was filtered to remove inorganic material and to obtain filtrate followed by drying the filtrate under reduced pressure. The residue was recrystallized from methylenechloride/ether to yield 1.2 g of a product (75.4%). The unreacted monomethoxypolyethyleneglycol was removed using a high performance liquid chromatography for collection (Prep. HPLC). MS(MALDI/TOF) indicated that the resulting material has an average molecular weight of 5,996 and monomethoxypolyethylene 5000-succinate as a starting material has an average molecular weight of 5,050. The mass difference (946) was identical with paclitaxel 2'-chloromethyl carbonate group. MS(MALDI/TOF) m/z 5996 (ave. M. Wt.); 1H NMR (300 MHz, CDCl$_3$) . 4.22–3.37 (m, mPEG), 5.77 (m, 2H, OCOOCH$_2$O), 5.46 (s, 1H, 2'-H)

<EXAMPLE>3

Synthesis of 2'-(tert-butyldimethylsilyl)-paclitaxel
(3)

500 mg of paclitaxel (0.586 mmol) was dissolved in 10 ml of anhydrous dichloromethane. 106.0 mg of tert-butyldimethylsilyl chloride (0.70 mmole) and 71.8 mg of immidazole (1.05 mmole) solution in 1 ml of N,N-dimethylformamide was added to the resulting solution, and the mixture was stirred for 6 hours. 20 ml of dichloromethane was added to the mixture to dilute and washed twice with 5% hydrochloric acid and washed once with water. The organic layer was dried over anhydrous magnesium sulfate to remove water and dried under reduced pressure to yield 540 mg of a product (95%). $^1$H NMR (300 MHz, CDCl$_3$) . 0.10 (s, 3H, —CH$_3$), 0.03 (s, 3H, —CH$_3$), –0.02 (s, 3H, —CH$_3$), –0.26 (s, 3H, —CH$_3$)

<EXAMPLE>4

Synthesis of 2'-(tert-Butyldimethylsilyl)-7-chloromethyloxycarbonyl-paclitaxel (4)

540 mg of 2'-(tert-butyldimethylsilyl)-paclitaxel (0.558 mmol) was dissolved in 10 ml of anhydrous dichloromethane. 107.9 mg of chloromethylchloroformate (0.837 mmol) was added to the resulting solution. 91.4 mg of pyridine (1.116 mmol) was slowly dropwise added and stirred for 12 hours. 20 ml of dichloromethane was added to the resulting mixture to dilute and washed with 5% hydrochloric acid (HCl) solution and saturated sodium bicarbonate solution. The organic layer was collected and dried over anhydrous magnesium sulfate to remove water followed by drying of the resulting material under reduced pressure to yield 572 mg of a product (97%). $^1$H NMR (300 MHz, CDCl$_3$). 5.98 (d, 1H, J=6.48 Hz), 5.70 (m, 1H), 5.51 (d, 1H, J=6.48 Hz), 0.00 (s, 3H, —CH$_3$), –0.01 (s, 3H, —CH$_3$), –0.03 (s, 3H, —CH$_3$), –0.30 (s, 3H, —CH$_3$)

<EXAMPLE>5

Synthesis of 7-chloromethyloxycarbonyl-paclitaxel (5)

572 mg of 2'-(tert-butyldimethylsilyl)-7-chlorooxycarbonyl-paclitaxel (0.54 mmol) was dissolved in 10 ml of acetonitrile. 10 ml of 1% hydrogen fluoride in acetonitrile was mixed with the resulting solution. The mixture was stirred for 30 minutes and evaporated under reduced pressure to remove acetonitrile. The resulting material was dissolved in 30 ml of diethylether and washed with a saturated sodium bicarbonate solution and distilled water followed by drying of the resulting material over anhydrous sodium sulfate to remove water and drying of it under reduced pressure to yield 456 mg of a product (91%). 1H NMR (300 MHz, CDCl$_3$) . 5.97 (d, 1H, J=6.47 Hz, OCOO CH$_2$Cl), 5.51 (d, 1H, J=6.40 Hz, OCOOCH$_2$Cl), 3.92 (d, 1H, J=6.77 Hz, 7-H); 13C NMR (75 MHz, CDCl$_3$) . 154.83 (O$\underline{C}$OOCH$_2$Cl)

<EXAMPLE>6

Synthesis of 7-mPEG 5000-succinyloxymethyloxycarbonyl-paclitaxel (6)

1 g of 7-chloromethyloxycarbonyl-paclitaxel (1.057 mmol) was dissolved in anhydrous benzene. 5.285 g of monomethoxypolyethyleneglycol 5000-succinate (1.057 mmol), 475 mg of sodium iodide (3.171 mmol), 262.8 mg of potassium carbonate (1.902 mmol) and 195.5 mg of 18-crown-6 ether (0.739 mmol) were mixed with the resulting solution. The mixture was stirred for 36 hours while refluxing and dried under reduced pressure to remove benzene and dissolved in 50 ml of dichloromethane. The obtained material was filtered to remove un-dissolved material. The organic layer was washed twice with water, the separated organic layer was dried over anhydrous magnesium sulfate to remove water, dried under reduced pressure and recrystallized from isopropyl alcohol to obtain a solid material. The solid material was purified with high performance liquid chromatography for collection (Prep. HPLC) to yield 433 mg of a pure product (68%). $^1$H NMR (300 MHz, CDCl$_3$) . 4.39–3.38 (m, mPEG), 5.88 (d, 1H, J=5.85 Hz, OCOO$\underline{CH_2}$O), 5.71 (d, 1H, J=5.85 Hz, OCOO$\underline{CH_2}$O)

<EXAMPLE>7

Synthesis of 7-polyethyleneglycol 6000-di (succinyloxymethyloxycarbonyl-paclitaxel) (7)

180 mg of 7-chloromethyloxycarbonyl-paclitaxel (0.19 mmol) was dissolved in 20 ml of anhydrous benzene. 570 mg of polyethyleneglycol 6000-disuccinate (0.095 mmol), 34 mg of sodium iodide (0.228 mmol), 79 mg of potassium carbonate (0.57 mmol) and 27 mg of 18-crown-6-ether (0.1 mmol) were mixed with the resulting solution. The mixture was stirred for 18 hours while refluxing and dried under reduced pressure to remove benzene followed by dissolving the resulting material in 10 ml of dichloromethane. The resulting material was filtered to remove un-dissolved material. The organic layer was washed twice with water and the separated organic layer was dried over anhydrous magnesium sulfate to remove water followed by drying of the resulting material under reduced pressure and by recrystallization of it to obtain a solid material. The solid material was purified with high performance liquid chromatography for collection (Prep. HPLC) to yield 560 mg of a pure product (42%). $^1$H NMR (300 MHz, CDCl$_3$) . 4.33–3.39 (m, PEG), 5.88 (d, 1H, J=5.79 Hz, OCOOCH$_2$O), 5.71 (d, 1H, J=5.79 Hz, OCOOCH$_2$O), 2.70 (m, 4h,CO$\underline{CH_2CH_2}$CO)

<EXAMPLE>8

Synthesis of 2'-monomethoxypolyethyleneglycol 20000-succinyloxymethyloxycarbonyl-paclitaxel (8)

2'-chloromethyloxycarbonyl paclitaxel (995 mg, 1.050 mmole) was dissolved in 150 ml of anhydrous benzene. Monomethoxypolyethylene glycol 20000-succinate (11.1 g, 1.1 mmole), sodium iodide (472. mg, 3.149 mmoles), potassium carbonate (261 mg, 1.888 mmoles), 18-crown-6 ether (396.5 mg, 1.5 mmole) were added to the resulting solution and the mixture was refluxed for 20 hours. The resulting mixture was cooled to room temperature and filtered to remove inorganic materials followed by drying the resulting material under reduced pressure. The resulting material was recrystallized from methylenechloride/ether. The recrystallized material was purified with high performance liquid chromatography (Prep. HPLC) to yield 13.4 mg of a pure product (60.7%); $^1$H NMR (300 MHz, CDCl$_3$) . 4.20–3.41 (m, mPEG), 5.77 (m, 2H, OCOO$\underline{CH_2}$O), 5.42 (s, 1H, 2'-H)

<EXAMPLE>9

Synthesis of 2'-polyethyleneglycol 20000-di (succinyloxymethyloxycarbonyl-paclitaxel) (9)

2'-chloromethyloxycarbonyl paclitaxel (995 mg, 1.050 mmole) was dissolved in 150 ml of anhydrous benzene. Polyethylene glycol 20000-dissucinate (5.5 g, 0.55 mmole), sodium iodide (472 mg, 3.149 mmoles), potassium carbonate (261 mg, 1.888 mmoles), 18-crown-6 ether (396.5 mg, 1.5 mmole) were added to the resulting solution and refluxed for 20 hours. The reaction mixture was cooled to room temperature and filtered to remove inorganic materials followed by the drying of the filtrate under reduced pressure. The resulting material was recrystallized from methylenechloride/ether. The resulting material was purified with high performance liquid chromatography for collection (Prep. HPLC) to yield 12.3 g of a pure product (53%); $^1$H NMR (300 MHz, CDCl$_3$) . 4.23–3.45 (m, mPEG), 5.79 (m, 2H, OCOOCH$_2$O), 5.50 (s, 1H, 2'-H)

<EXAMPLE>10

Synthesis of 7-monomethoxypolyethyleneglycol 20000-succinyloxymethyloxycarbonyl-paclitaxel (10)

7-chloromethyloxycarbonyl paclitaxel (995 mg, 1.050 mmole) was dissolved in 150 ml of anhydrous benzene. Monomethoxypolyethyleneglycol 20000-succinate (11.1 g, 1.1 mmole), sodium iodide (472. mg, 3.149 mmoles), potassium carbonate (261 mg, 1.888 mmoles), and 18-crown-6 ether (396.5 mg, 1.5 mmole) were added to the resulting solution and refluxed for 20 hours. The resulting mixture was cooled to room temperature and filtered to remove inorganic material followed by the drying of filtrate under reduced pressure. The resulting material was recrystallized from methylenechloride/ether. The recrystallized material was purified with high performance liquid chromatography for collection (Prep. HPLC) to yield 14.6 g of a pure product (66%); $^1$H NMR (300 MHz, CDCl$_3$) . 4.21–3.37 (m, mPEG), 5.89 (d, 1H, J=5.78 Hz, OCOOC$\underline{H}_2$O), 5.74 (d, 1H, J=5.78 Hz, OCOOC$\underline{H}_2$O), 5.46 (s, 1H, $\overline{2'\text{-H}}$)

<EXAMPLE>11

Synthesis of 7-polyethyleneglycol 20000-di (succinyloxymethyloxycarbonyl-paclitaxel (11)

7-chloromethyloxycarbonyl paclitaxel (995 mg, 1.050 mmole) was dissolved in 150 ml of anhydrous benzene. Monomethoxypolyethyleneglycol 20000-succinate (5.5 g, 0.55 mmole), sodium iodide (472. mg, 3.149 mmoles), potassium carbonate (261 mg, 1.888 mmoles), and 18-crown-6 ether (396.5 mg, 1.5 mmole) were added to the resulting solution and refluxed for 20 hours. The resulting mixture was cooled to room temperature and filtered to remove inorganic materials followed by the drying of filtrate under reduced pressure. The resulting material was recrystallized from methylenechloride/ether. The recrystallized material was purified with high performance liquid chromatography for collection (Prep. HPLC) to yield 13.3 g of a pure product (57.5%); 1H NMR (300 MHz, CDCl$_3$) . 4.22–3.37 (m, mPEG), 5.91 (d, 1H, J=5.80 Hz, OCOOC$\underline{H}_2$O), 5.74 (d, 1H, J=5.78 Hz, OCOOC$\underline{H}_2$O), 5.46 (s, 1H, $\overline{2'\text{-H}}$)

<EXAMPLE>12

Synthesis of 7-monomethoxypolyethyleneglycol 5000-succinylthiomethyloxy carbonyl-paclitaxel)

7-chloromethyloxycarbonyl-paclitaxel (2 g, 2.114 mmole) was dissolved in 150 ml of anhydrous benzene. Monomethoxypolyethyleneglycol 5000-succinylthionate (5.29 g, 1.057 mmole), sodium iodide (475 mg 3.171 mmol), potassium carbonate (262.8 mg, 1.902 mmoles), and 18-crwon-6 ether (396.5 mg, 1.5 mmole) were mixed with the resulting solution. The mixture was stirred for 36 hours while refluxing and dried under reduced pressure to remove benzene followed by dissolving the resulting material in 50 ml of dichlromethane. The resulting material was filtered to remove un-dissolved material. The organic layer was washed twice with water and the separated organic layer was dried over anhydrous magnesium sulfate to remove water and dried under reduced pressure followed by the recrystallization of the dried material from isopropyl alcohol to obtain a solid material. The solid material was purified with high performance liquid chromatography for collection (Prep. HPLC) to obtain 9.2 g of pure product (72%). $^1$H NMR (300 MHz, CDCl$_3$) . 4.39–3.38 (m, mPEG), 5.98 (d, 1H, J=5.85 Hz, OCOOC$\underline{H}_2$S), 5.81 (d, 1H, J=5.85 Hz, OCOOC$\underline{H}_2$), 5.44 (s, 1H, $\overline{2'\text{H}}$)

1) Solubility Test

The prodrug compounds according to Examples 2, 6 to 12 were added and dissolved in 1 ml of distilled water followed by the measurement of haze with a Hazemeter (NHD-300A, Nippon denshoku IND.) according to the increase in the amount of the prodrug compound. The solubility was defined by the amount of the prodrug compound at which the fluidity occurs and the haze is 0.5 or less than. The results are presented in Table 1.

TABLE 1

| Prodrug | Amount of dissolving |
| --- | --- |
| Example 2 | 400 mg or more |
| Example 6 | 400 mg or more |
| Example 7 | 400 mg or more |
| Example 8 | 400 mg or more |
| Example 9 | 400 mg or more |
| Example 10 | 400 mg or more |
| Example 11 | 400 mg or more |
| Example 12 | 400 mg or more |

As shown in Table 2, the prodrug compounds of Examples 2, 6 to 12 had water-solubility of 400 mg or more and exhibited improved water-solubility.

2) Hydrolysis of Prodrug Compound 10 ml of rat plasma was precisely balanced in a 37 . water bath and the prodrug compounds of Examples 2 and 6 were added in the water bath and dissolved (the amount of paclitaxel included in the prodrug compound was corresponded to 0.5 mg). At each time (0, 0.5, 1, 1.5, 2, 2.5, 3, 4, 5, 10 minutes), 100. of each the solution was withdrawn from the solution and admixed to a 200. of acetonitrile-included tub, and centrifuged at 11,000 rpm for 5 minutes followed 200. of the obtained supernatant was analyzed with a high performance liquid chromatography (HPLC). The hydrolysis tests on human plasma, phosphate buffer solution and distilled water were performed as like the test in rat plasma, the same in the phosphate buffer solution and distilled water was collected at 24 hours intervals. The hydrolysis half life time in the buffer solution, rat plasma, human plasma and distilled water were measured and the results are presented in Table 2.

TABLE 2

| | $T_{1/2}$ Hydrolysis | | | |
| --- | --- | --- | --- | --- |
| | PBS buffer solution (pH 7.4) | Rat plasma (pH 7.3) | Human plasma (pH 6.8) | Distilled water (pH 6.0) |
| Example 2 | 28.6 hours | 1.12 minutes | 2.56 minutes | 232.8 hours |
| Example 6 | 26.7 hours | 0.94 minutes | 2.31 minutes | 201.5 hours |

It was shown from Table 2 that the half life time of the prodrug compound of Examples 2 and 6 exhibited 2 minutes in rat plasma, and about 3 minutes in human plasma. Whereas, the hydrolysis rate without esterase exhibited 26 hours and 200 hours or more in phosphate butter solution (PBS buffer) and distilled water, respectively.

Figure 1:
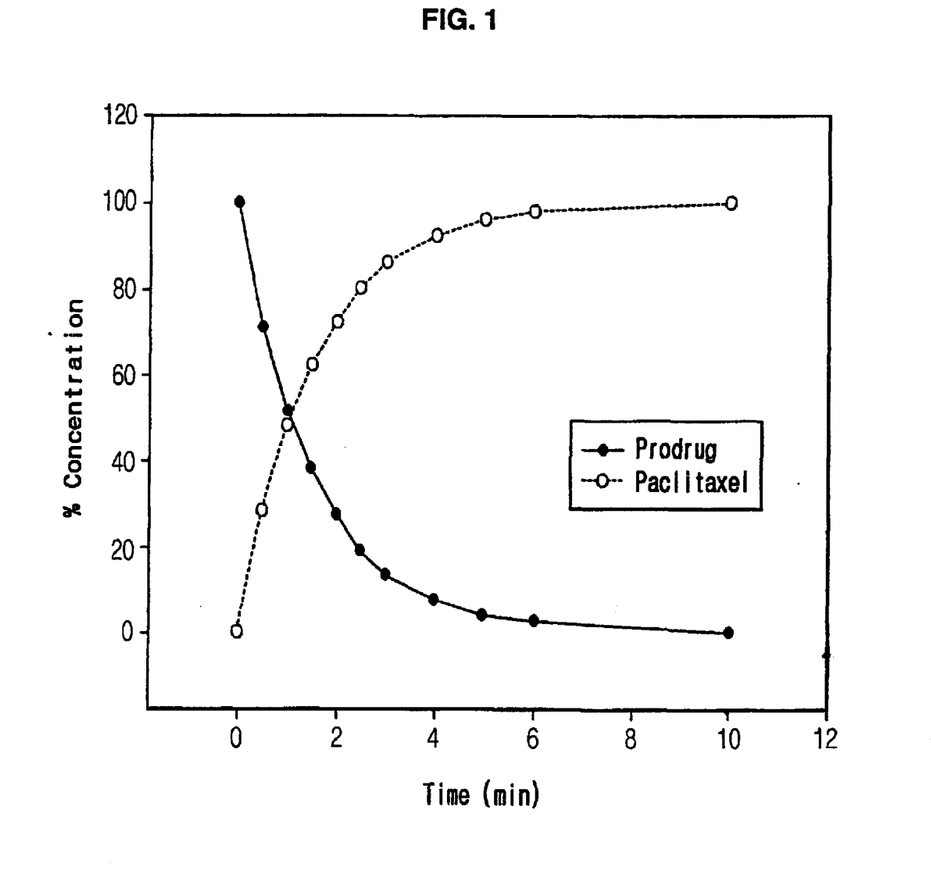
FIG. 1 is a graph showing hydrolysis results according to time of 2'-monomethoxy poly ethylene glycol 5000-succinyloxymethyloxycarbonyl-paclitaxel of Example 2 in 37. rat plasma.
Figure 2:
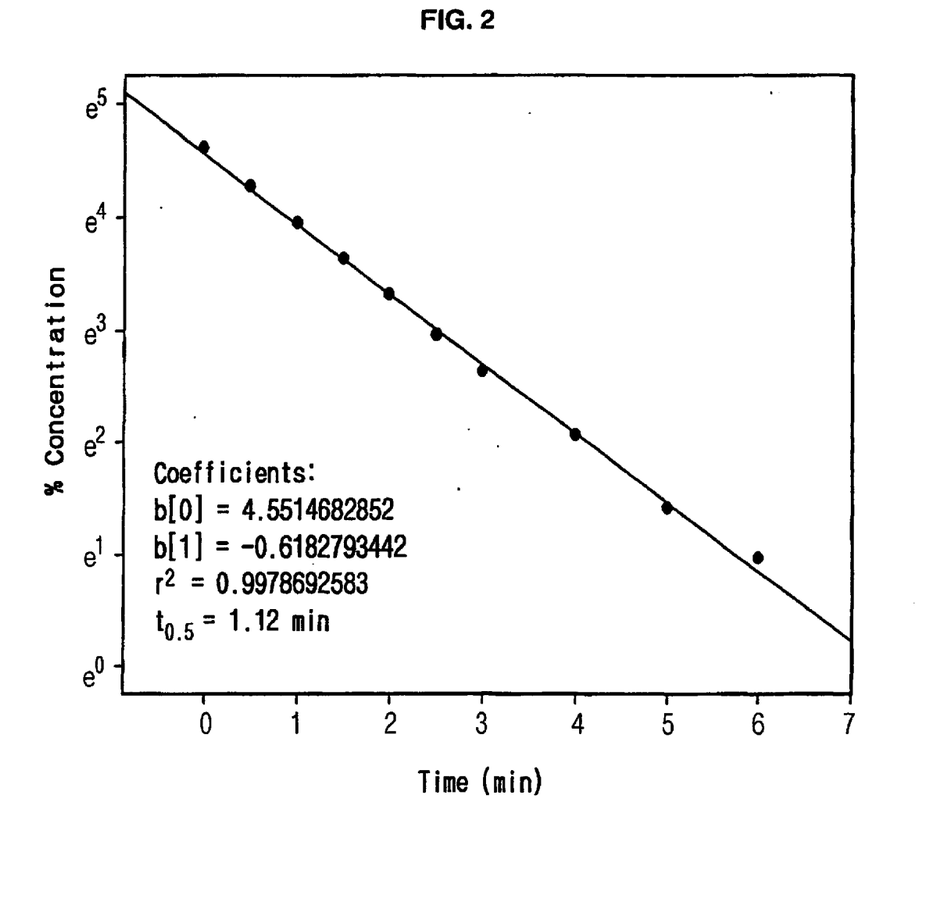
FIG. 2 is a linear graph showing hydrolysis results according to time of 2'-monomethoxy poly ethylene glycol 5000-succinyloxymethyloxycarbonyl-paclitaxel in 37. rat plasma.
Figure 3:
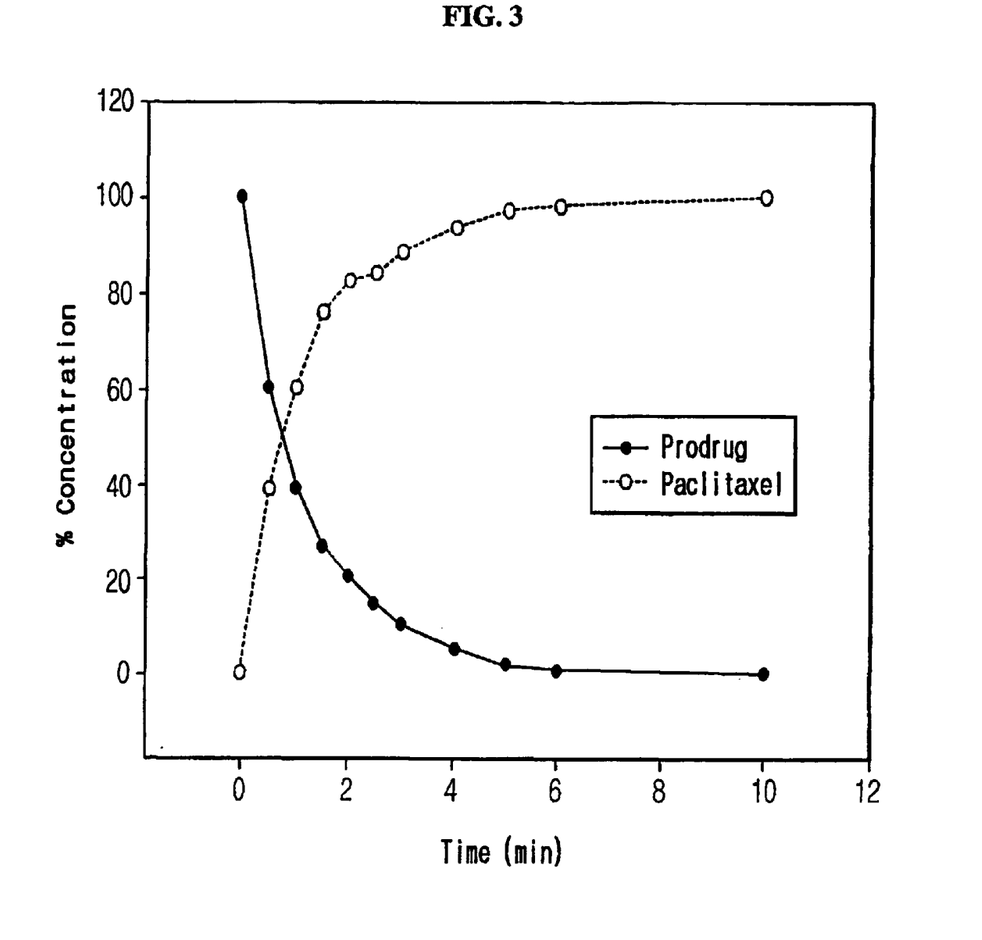
FIG. 3 is a graph showing hydrolysis result according to time of 7-monomethoxy poly ethylene glycol 5000-succinyloxymethyloxycarbonyl-paclitaxel in 37. rat plasma.
Figure 4:
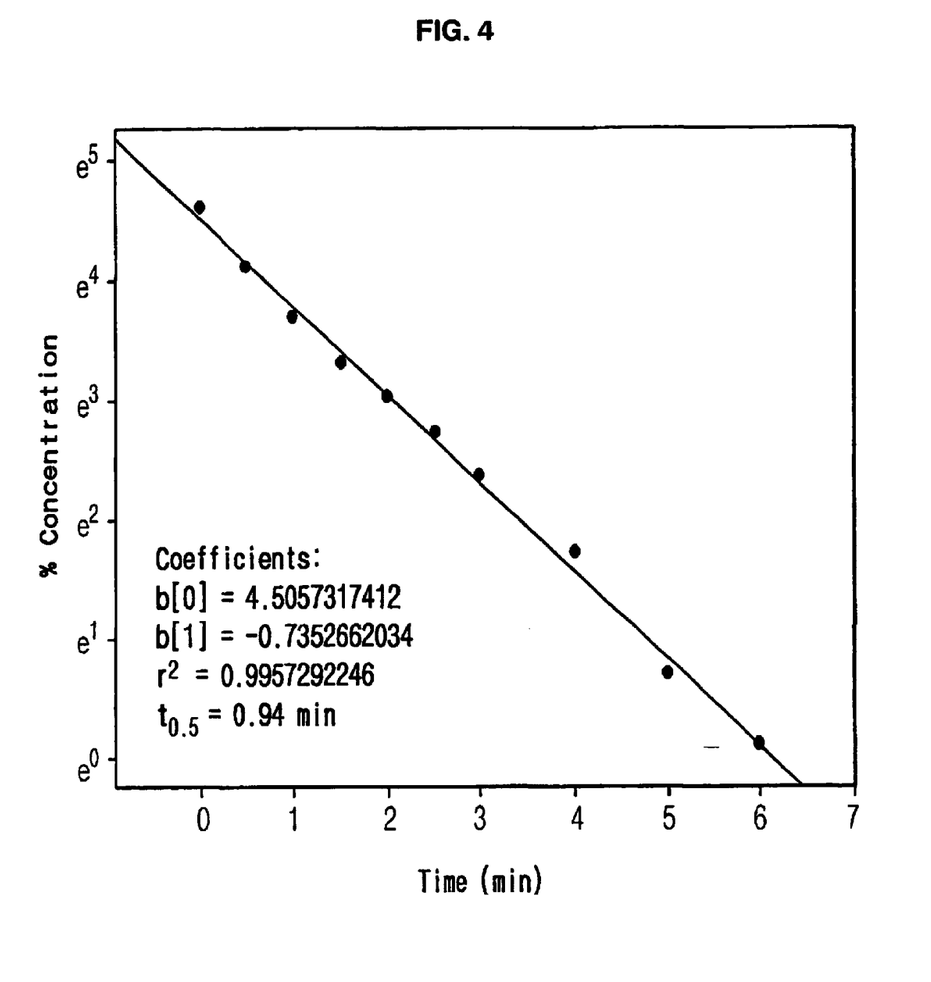
FIG. 4 is a linear graph showing hydrolysis result of 7-monomethoxy poly ethylene glycol 5000-succinyloxymethyloxycarbonyl-paclitaxel according to Example 6 in 37. rat plasma.

In order to identify the conversion rate from the prodrug compound of Examples 2 and 6 to paclitaxel, the concentration of the prodrug and paclitaxel in the sample were measured after which the results are shown in FIGS. 1 and 3, respectively. In addition, the linear graphs showing these results are presented in FIGS. 2 and 4, respectively. As shown in FIGS. 1 to 4, at least 50% of the prodrug compound of Examples 2 and 6 was converted to paclitaxel within about 2 minutes and 100% thereof was converted to paclitaxel within 10 minutes.

What is claimed is:

1. A water-soluble prodrug compound comprising moiety of paclitaxel or derivatives thereof, represented by formula 1:

<Formula 1>

(wherein,
R is formulas a or b,

<Formula a>

<Formula b>

D represents a moiety of paclitaxel or derivatives thereof,
M is an integer of 1 to 6, n is an integer of 10 to 1,000,
X represents O, S or NH, and
R' represents H or $CH_3$).

2. The water-soluble prodrug compound of claim 1 wherein the derivatives of paclitaxel is docetaxel.

3. The water-soluble prodrug compound of claim 1 wherein the m is an integer of 1 to 3.

4. The water-soluble prodrug compound of claim 1 wherein the n is an integer of 10 to 460.

5. The water-soluble prodrug compound of claim 4 wherein the n is an integer of 40 to 230.

6. A method of preparing a water-soluble prodrug compound including moiety of paclitaxel or derivatives thereof, represented by formula 1 comprising:
reacting a compound of formula 2 with a polyethylene glycol derivative of formula 3:

<Formula 1>

<Formula 2>

<Formula 3>

(wherein,
R is formulas a or b,

<Formula a>

<Formula b>

D represents a moiety of paclitaxel or derivatives thereof,
m is an integer of 1 to 6, n is an integer of 10 to 1,000,
X represents O, S or NH,
R' represents H or $CH_3$, and
Y is a suitable leaving group such as halogen.).

7. The method of claim 6 wherein the compound of formula 2 is prepared by esterifying paclitaxel or derivatives thereof with a compound of formula 4:

<Formula 4>

(wherein,
R' represents H or $CH_3$, and
Y is a suitable leaving group such as halogen).

8. The method of claim 6 wherein the compound of formula 2 is prepared by
reacting paclitaxel or derivatives thereof with a silyl agent to prepare a compound of formula 5;
reacting the compound of formula 5 with a compound of formula 4 to prepare a compound of formula 6; and
deprotecting the compound of formula 6 with a weak acid:

<Formula 4>

<Formula 5>

<Formula 6>

(wherein,
$R_1$ is $C_6H_6$ or $(CH_3)_3CO$,
$R_2$ is $CH_3CO$ or H,
Pt is a silyl protecting group,
D' is moiety of the compound of formula 5,
R' is H or $CH_3$, and
Y is a suitable leaving group such as halogen).

9. The method of claim 6 wherein the esterifying step is performed in the presence of base.

10. The method of claim 6 wherein the step of reacting the compound of formula 2 with the compound of formula 3 is performed in the presence of a reaction-accelerating catalyst, base and a cation capture.

11. A pharmaceutical composition comprising a water-soluble compound comprising a moiety of paclitaxel or derivatives thereof, represented by formula 1, as an active ingredients:

<Formula 1>

(wherein,
R is formulas a or b,

OCH₃ <Formula a>

<Formula b>

D represents moiety of paclitaxel or derivatives thereof,
m is an integer of 1 to 6, n is an integer of 10 to 1,000,
X represents O, S or NH, and
R' represents H or $CH_3$).

12. The pharmaceutical composition of claim 11 wherein the derivatives of paclitaxel is docetaxel.

* * * * *